United States Patent [19]
Sheldon et al.

[11] Patent Number: 5,084,038
[45] Date of Patent: Jan. 28, 1992

[54] APPARATUS AND A METHOD FOR FORMING TAMPONS AND THE TAMPON ITSELF

[75] Inventors: Donald A. Sheldon, Appleton; Paul G. Franke, Menasha, both of Wis.; Raymond Brown, Shepperton, England

[73] Assignee: Kimberly-Clark Corporation, Neenah, Wis.

[21] Appl. No.: 406,655

[22] Filed: Sep. 12, 1989

[51] Int. Cl.⁵ ............................................. A61F 13/15
[52] U.S. Cl. ........................................ 604/358; 604/904; 156/193; 156/194; 28/118; 28/119; 28/120
[58] Field of Search ................. 604/904, 358; 28/118-120; 156/193, 194

[56] References Cited

U.S. PATENT DOCUMENTS

| | | | |
|---|---|---|---|
| 271,625 | 2/1883 | Goff | 604/904 |
| 2,529,183 | 11/1950 | Parish | 128/285 |
| 2,553,000 | 5/1951 | Parish | 128/285 |
| 2,581,561 | 1/1952 | Shaw | 18/56 |
| 4,302,174 | 11/1981 | Hinzmann | 425/341 |
| 4,318,407 | 3/1982 | Woon | 128/285 |
| 4,624,668 | 11/1986 | Siegers | 604/904 |
| 4,642,108 | 2/1987 | Sustmann | 604/379 |
| 4,755,164 | 7/1988 | Hinzmann | 493/288 |
| 4,816,100 | 3/1989 | Friese | 156/191 |
| 4,836,587 | 6/1989 | Hinzman | 289/2 |

FOREIGN PATENT DOCUMENTS

| | | |
|---|---|---|
| 614475 | 2/1961 | Canada . |
| 3347649 | 7/1985 | Fed. Rep. of Germany . |

Primary Examiner—David J. Isabella
Assistant Examiner—K. Reichle
Attorney, Agent, or Firm—Thomas J. Connelly

[57] ABSTRACT

An apparatus and a method for forming tampons is disclosed, as well as the tampon itself. The apparatus includes a mechanism and the method includes the step of advancing and cutting a cover strip and an absorbent ribbon into predetermined lengths. A portion of the absorbent ribbon is then overlapped by the cover strip and both are radially wound into a cylinder having a length equal to at least two tampons. The cylinder is then compressed and cut into two or more single length pledgets. The single length pledgets are heat set before a withdrawal string is attached to form a finished tampon. The tampon itself can be made with tucked or untucked ends.

33 Claims, 6 Drawing Sheets

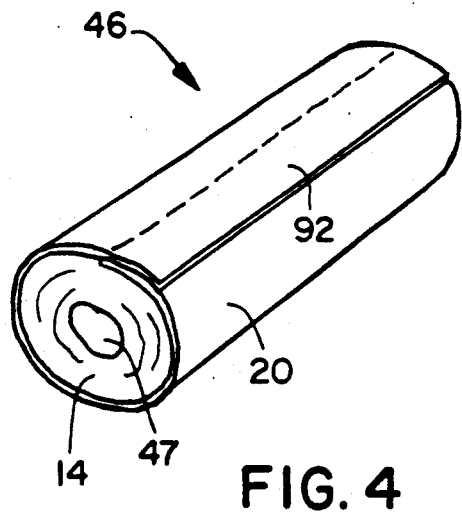
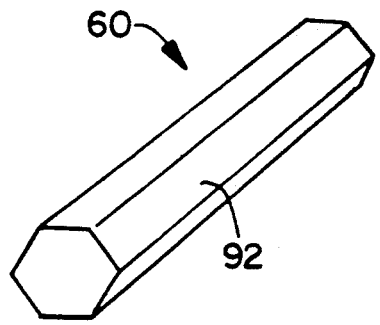
FIG. 4  FIG. 5
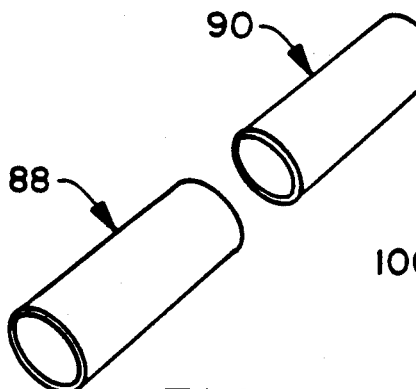
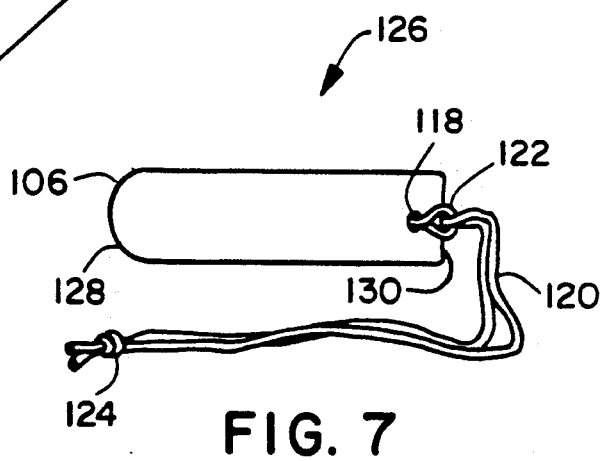
FIG. 6  FIG. 7
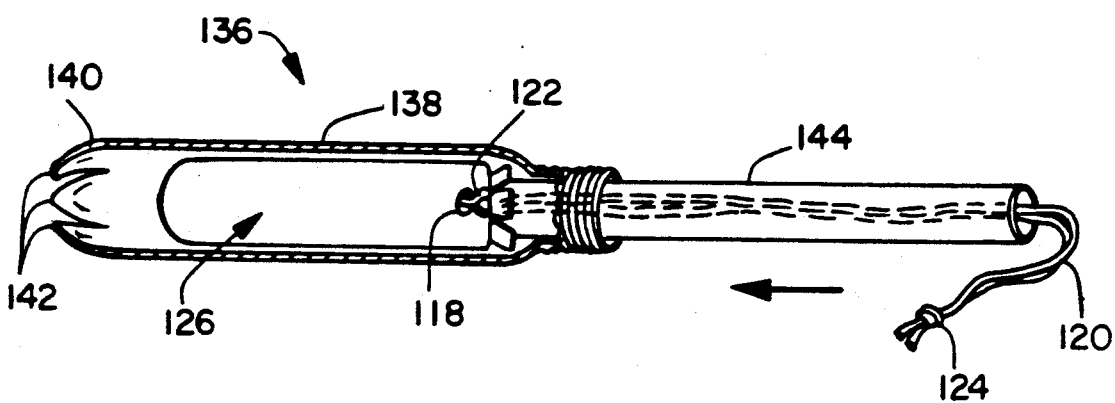
FIG. 8

APPARATUS AND A METHOD FOR FORMING TAMPONS AND THE TAMPON ITSELF

FIELD OF THE INVENTION

This invention relates to an apparatus and a method for more efficiently forming tampons and also to tampons formed by this method.

BACKGROUND OF THE INVENTION

Currently, there are two basic types of tampons used for feminine hygiene. The first type is a digitally insertable tampon which is designed to be inserted directly by the user's fingers. The second type is an applicator style tampon which is designed to be inserted with the aid of an applicator. Both types are usually made by folding or rolling a loosely associated rectangular strip of absorbent material into a blank and then compressing the blank into a cylindrically shaped product known as a pledget. The pledget may or may not have a cover, depending upon the manufacturer. In both types, a withdrawal string is attached to the pledget before the tampon is wrapped and packaged for sale. In the applicator style tampon, the tampons are assembled into an applicator prior to being wrapped and packaged.

Up until now, tampons have been normally manufactured in either an in-line process or in an intermittent indexing type operation. Some representative methods of forming tampons and the apparatuses associated with these methods are disclosed in U.S. Pat. Nos. 4,816,100; 4,624,668; 4,642,108; and German Patent No. DE 3,347,649.

Most current processes operate at speeds which are considered slow by today's standards. With the increase in labor costs and competition, it is necessary for manufacturers to be able to significantly increase the speed at which tampons can be made. It is also beneficial if manufacturers can utilize a major portion of their existing machinery while increasing the process speed.

Since most tampon manufactures have not even considered cutting an elongated pledget into two or more single length pledgets, there is very little prior art. However, in U.S. Pat. No. 4,755,164 a method is disclosed for forming hollow applicator tubes by cutting the tubes in half. An applicator tube is different from a tampon in that it is usually constructed of thick paper or plastic, is not designed to remain in a woman's vagina, and does not contain a fibrous core. Two other patents which relate to slicing an article in half include U.S. Pat. No. 271,625 and Canadian Patent No. 614,475. In both of these patents, only the outer cover of a tampon is sliced in half while the fibrous core is left uncut.

German Patent No. 3,347,649, cited above, teaches a tampon wherein the cover strip is narrower than the width of the absorbent. This patent also shows, in FIG. 6, a tampon wherein the insertion end is uncovered by the cover strip while the retrieval end has the cover strip positioned tangent to it.

Now an apparatus and a method have been developed which can produce unique tampons quickly, efficiently and at a cheaper cost.

SUMMARY OF THE INVENTION

Briefly, the present invention relates to an apparatus and a method for forming tampons and to the tampon itself. The apparatus includes a mechanism for advancing and individually cutting a cover strip and an absorbent ribbon into defined lengths. An individual length of cover strip is then overlapped onto a portion of an individual length of absorbent ribbon and is attached thereto such as by heat and/or pressure. Both strips are then rolled into a cylinder with the cover strip encircling the outer circumference thereof. The cylinder is compressed into an elongated pledget and is then cut into at least two single length pledgets. The apparatus further includes a heat setting device and a means for attaching a withdrawal string approximate one end of the tampon.

The method includes the steps of positioning a liquid permeable cover strip over a portion of a non-woven absorbent ribbon, both of which have a defined length and width. The cover strip is attached to the ribbon at the overlapped portion and both are rolled into a cylinder with the cover strip encircling the outer circumference thereof. The cylinder will have a length corresponding to the length of at least two finished tampons. The elongated cylinder is compressed into a pledget which is then cut into at least two single length pledgets. Each single length pledget is heat set to a desired configuration before having a withdrawal string attached thereto. The finished pledget can be wrapped or assembled into an applicator before being shipped to the ultimate consumer.

The tampon comprises a radially wound non-woven absorbent ribbon circumferentially surrounded by a liquid permeable cover strip. Both the ribbon and cover strip are compressed into a cylindrical shape having first and second oppositely aligned ends wherein the ribbon is exposed on either one or both ends. The absorbent ribbon is sized relative to the cover strip such that finished tampons can be manufactured with tucked or untucked ends, or with a cylindrical cuff if desired.

The general object of this invention is to provide an apparatus and a method for continuously forming tampons. A more specific object of this invention is to provide an apparatus and a method for forming two or more tampons from a single elongated pledget.

Another object of this invention is to provide an apparatus and a method for forming multiple tampons at a high rate of speed, more efficiently and at a lower cost compared to present day processes.

Still, another object of this invention is to provide a tampon having a unique configuration wherein one or both ends exhibits exposed absorbent ribbon.

Still further, an object of this invention is to provide a tampon wherein one end can be covered by having the cover strip tucked into the absorbent ribbon.

Other objects and advantages of the present invention will become more apparent to those skilled in the art in view of the following description an the accompanying drawings.

BRIEF DESCRIPTION OF THE DRAWINGS

FIG. 4 is a perspective view of a softwind, double length cylinder showing a large opening formed through the absorbent and showing the cover strip as having an unattached tail portion.

FIG. 5 is a perspective view of a compressed, elongated pledget having a hexagonal shape.

FIG. 6 is a perspective view of two single length pledgets which have undergone heat set and have acquired a circular cross-sectional shape.

FIG. 7 is a side view of a finished tampon showing an aperture diametrically formed therethrough and having a withdrawal string inserted therethrough and looped about itself so as to form a secured attachment.

FIG. 8 is a perspective view of a tampon produced according to this invention and assembled into a tampon applicator.

DETAILED DESCRIPTION OF THE PREFERRED EMBODIMENTS

Figure 1:
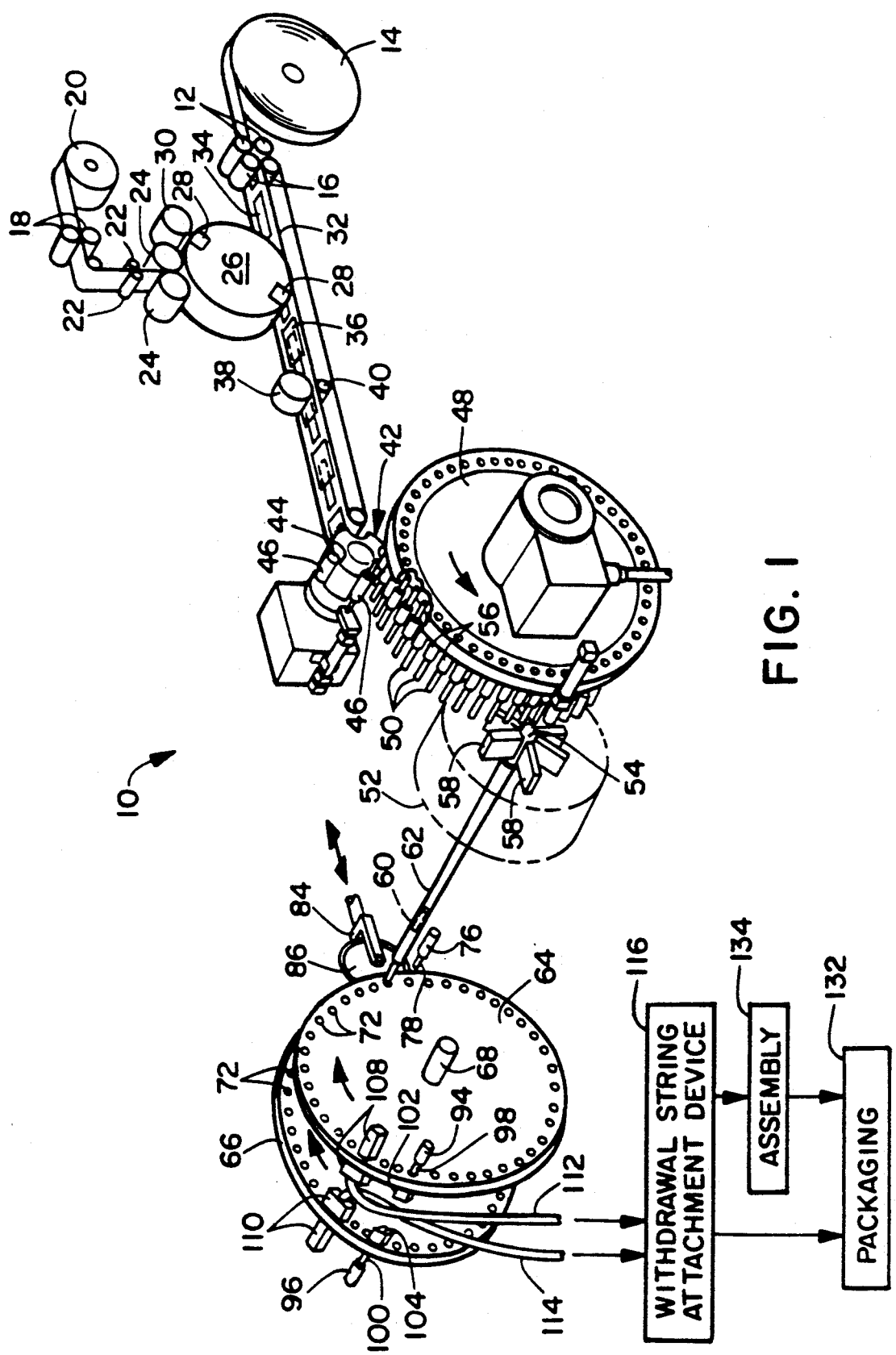
FIG. 1 is a schematic view of an apparatus for forming tampons at high speeds.

Referring to FIG. 1, an apparatus 10 is shown for continuously forming tampons at high speeds and in an efficient manner. The apparatus 10 includes a set of rollers 12 which grasp and advance a continuous supply of absorbent ribbon 14. The absorbent ribbon 14 can be any suitable absorbent material made from artificial or natural fibers including polyester, cellulose, acetate, nylon, polypropylene, rayon, cotton or blends thereof. The absorbent ribbon 14 can also be a nonwoven, bonded carded web comprised of between about 70 and 95% rayon and about 5 to 30% cotton. Normally, the fibers are formed by convolutely winding multiple fibers into a ribbon form. The absorbent ribbon 14 can have a width of one or more inches (about 25 or more millimeters) but when two pledgets are to be formed from a single width, the width should preferably be between 4 and 6 inches (about 100 to 150 millimeters).

The absorbent ribbon 14 should have two longitudinal side edges which are approximately parallel to one another.

The absorbent ribbon 14 is directed through a second set of rollers 16 which continuously rotate. The first set of rollers 12 can be programmed to stop and start at certain intervals such that the action between the two sets of rollers 12 and 16 will cause the ribbon 14 to tear into a defined length. The length of the ribbon 14 will vary depending upon the desired weight and/or diameter of the finished tampon. However, for most applications, a length of between 6 to 12 inches (about 150 to 300 millimeters), and preferably around 9 to 11 inches (about 225 to 275 millimeters) is satisfactory. The cut ribbon 14 should have a generally rectangular configuration.

The apparatus 10 also contains a set of rollers 18 which can grasp and advance a continuous supply of a cover strip 20. The cover strip 20 can be constructed of natural or synthetic materials which are preferably liquid permeable. The cover strip 20 can be a powder bonded carded web made from 0-100% rayon, 0-100% polyester, 0-100% cotton or it can be made of another type of polymer, or a blend thereof. The cover strip 20 could also be made from cottonwool. A particular useful blend for the base material is about 85% polyester and about 15% rayon. A binder is usually added to the base material to give the cover strip 20 adhesion properties so that it will bond to the absorbent ribbon 14 as well as to itself at the overlap areas. A particularly useful powder binder is about 10-25% polyester powder, preferably about 15-20%. The powder binder can be obtained from Bonar Fabrics Corporation, 50 Arcadia Drive, P.O. Box 3745, Greenville, S.C., 29608.

After passing between the rollers 18, the cover strip 20 is routed between the nip of a pair guide rollers 22 and then pass a pair of feed rolls 24. The feed rolls 24 direct the cover strip 20 onto a transfer roll 26 which contains a pair of anvils 28 arranged on it's inner circumference. A cutter roll 30 is positioned adjacent to the outer periphery of the transfer roll 26 and downstream of the feed rolls 24. The cutter roll 30 is synchronized so as to line up with the anvils 28 and will cut the cover strip 20 into generally rectangular segments having approximately parallel longitudinal side edges. The cover strip 20 will have a defined length, preferably between 5 and 8 inches (about 125 to 200 millimeters). The width of the cover strip 20 can be varied so as to be longer, shorter or equal to the width of the absorbent ribbon 14. The particular width of the cover strip 20 will impact upon the final configuration of the finished tampon.

The individual lengths of the cover strips 20 can be held onto the outer circumference of the transfer roll 26 by vacuum. The transfer roll 26 is rotated clockwise and will contact a continuous belt 32 which is used to transport individual segments 34 of the absorbent ribbon 14. Preferably, the individual segments 34 have a basis weight of at least 100 grams per square meter. As the individual segments 34 pass under the transfer roll 26, the speed of the transfer roll 26 can be adjusted such that a portion of an individual cover strip 20 will overlap a portion of the individual absorbent segment 34. At this point, the vacuum is turned off and the cover strip 20 will separate from the transfer roll 26. The combination absorbent ribbon and cover strip, denoted 36, is passed between the nip of a heated roll 38 and an anvil roll 40. The heated roll 38 can have a knurled or tooth shaped pattern formed on a portion of it's periphery so as to impinge upon the cover strip 20 and press it against the surface of the absorbent ribbon 14. The use of heat and/or pressure will cause the cover strip 20 to bond to the absorbent ribbon 14. The heat will activate the binder which is present within the cover strip 20 to assure that a secure bond is formed. However, it is possible to bond the cover strip 20 to the absorbent ribbon 14 by using just pressure, such as by passing the combination 36 between a pin roll and an apertured roll. Likewise, the combination 36 could be bonded together by just using heat or by using other types of bonding such as ultrasonic energy, laser beam, etc.

The particular area over which the cover strip 20 overlaps the absorbent ribbon 14 will depend upon the preference of individual manufacturers. It should be noted, however, that a smaller overlapped area may mean that the equipment must be synchronized more precisely. It should also be noted that the heated roll 38, with its knurled or tooth profile, can first contact the absorbent ribbon 14 before engaging the cover strip 20, if this is desireable. Likewise, it is also possible to construct the heated roll 38 such that it will bond only a portion of the overlapped cover strip 20 to the absorbent ribbon 14, instead of bonding over the entire length and/or width of the overlapped section.

Figure 14:
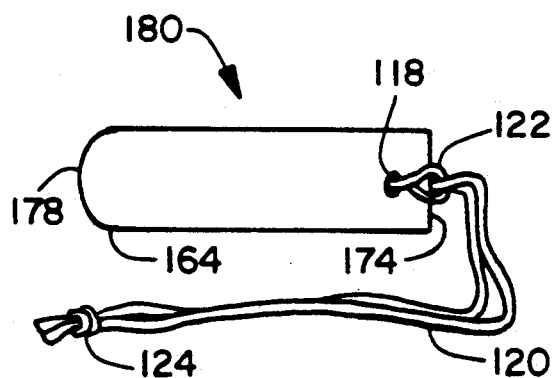
FIG. 14 is a side view of a pledget having a rounded insertion end and having a withdrawal string secured to the trailing end.
Figure 15:
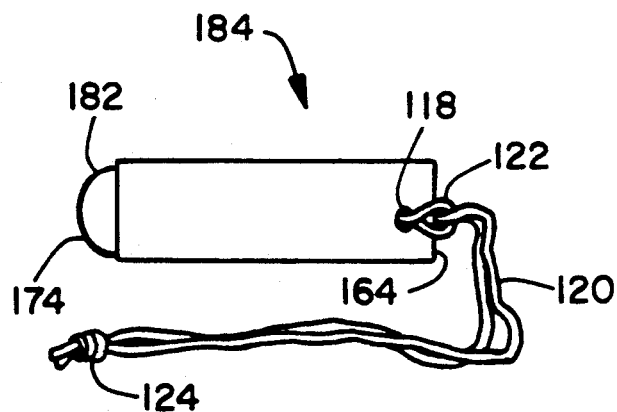
FIG. 15 is a side view of a pledget showing a rounded insertion end exhibiting exposed absorbent ribbon and a trailing end which is completely covered.

The absorbent ribbon 14 with its bonded cover strip 20 is advanced by the continuous belt 32 and is brought into contact with a first turret 42. The first turret 42 contains a plurality of mandrels 44 arranged in a circle which can individually rotate. The first turret 42 is driven by a mechanism which will permit it to index a predetermined amount as it rotates through each complete revolution. For purposes of illustration, the first 42 turret is shown as rotating counterclockwise. Each mandrel 44 has a plurality of small ports formed in its outer periphery which communicate with a source of vacuum so as to provide a means for grasping the end of the absorbent ribbon 14. The ribbon 14 is radially wound into a cylinder 46, see FIG. 4, which is commonly referred to as a "softwind". The diameter of the softwind cylinder 46 should be less than the opening of the mold cavity into which it is to be inserted. Typical diameters for the cylinder 46 is about 1 to 2 inches (about 25 to 50 millimeters) and the diameter of the hollow opening formed therein is about ¾ to 1 inch (about 18 to 25 millimeters). A good illustration of a softwind is shown in FIGS. 4, 8 and 14.

In situations where the width of the cover strip 20 is approximately equal to or less than the width of the absorbent ribbon 14, there is no need for a tucking operation. However, when the cover strip 20 has a width larger than the width of the absorbent ribbon 14, as is depicted in FIG. 8, then a tucking operation is required. The tucking operation will fold the sleeve portion of the cover strip 20, which extends beyond each end of the absorbent ribbon 14, into the hollow opening of the cylindrical softwind 46. The first tucking operation, when needed, will occur when the softwind 46 is positioned on the mandrel 44. Each mandrel 44 contains a central passageway which terminates at a distal outer end. Once the cylinder 46 is wound onto the mandrel 44, a vacuum is applied through the passageway to pull the sleeve portion of the cover strip 20 into the central opening formed in the softwind 46 and tuck it, thereby covering the absorbent ribbon 14. Each cylinder 46 is then transferred from the first turret 42 to a second turret 48 while both turrets are momentarily stopped.

The second turret 48 is designed to rotate in an indexing fashion just like the first turret 42 and also contains a plurality of mandrels 50. Each of the mandrels 50 has a central passageway which terminates into an exposed port located in the outer end thereof which communicates with a source of vacuum. As the second turret 48 is indexed to a desired position, a vacuum will be applied to pull the sleeve portion of the cover strip 20 into the opposite end of the softwind 46 and tuck it into the opening formed therein. In this fashion, both ends of the cover strip 20 can be tucked into the softwind 46.

It should be noted that the diameter of each of the mandrels 50 will be slightly smaller than the diameter of the opening formed in the cylindrical softwind 46. This size difference is beneficial for it prevents the first tuck from being destroyed as the softwind 46 is transferred to the mandrel 50.

As depicted in FIG. 1, the second turret 48 will rotate counterclockwise in an indexing fashion such that each of the mandrels 50 will come into alignment with a compressor 52. The compressor 52 contains a mold cavity 54 which will sequentially receive the softwinds 46 as they are transferred from the mandrels 50. One means of ejecting the softwinds 46 from the second mandrel 50 is to use a push-off spool 56 which is coaxially aligned and moveable with respect to each mandrel 50. The push-off spools 56 can be mechanically, electrically, pneumatically or hydraulically activated so as to transfer the softwind 46 into the mold cavity 54. The compressor 52 operates in a unique fashion, as is explained in U.S. Ser. No. 07/383,129 filed July 20, 1989, now U.S. Pat. No. 4,951,368 and entitled "Apparatus For Compressing Materials". This U.S. patent application is commonly assigned and is incorporated by reference and made a part hereof.

In general, the compressor 52 includes a plurality of dies 58 which reciprocate relative to one another so as to form the mold cavity 54 therebetween. When the softwind 46 is positioned within the mold cavity 54, the front and back gates of the compressor 52 will be closed thereby forming a closed cavity. The dies 58 will then be actuated so as to move towards one another and compress the softwind 46. The softwind 46 can be compressed a desired amount, for example at least 25%, preferably in the range of 50 to 200%, and most preferably in a range of about 100 to 150% of the initial diameter of the softwind 46. The compression will cause the softwind to be reduced in diameter to a fraction of its original diameter, for example to approximately ¼ of its original diameter. In the formation of tampons, the compressed material, which is known as a pledget, will usually have a diameter of less than ½ of an inch (about 12 millimeters).

Referring to FIG. 5, a good representation of an elongated pledget 60 is shown. The elongated pledget 60 is shown having a hexagonal configuration which is formed by a compressor containing six dies 58 arranged in a circular fashion and positioned approximately 60° apart. However, the cross-sectional configuration of the elongated pledget 60 can vary depending upon the number of dies 58 being used in the compressor 52 and the surface shape of each of the dies 58. For example, a triangular cross-sectional configuration could be formed by using three dies or a square cross-sectional configuration could be obtained by using four dies. If the dies 58 had concave surfaces, a circular cross-sectional configuration could be obtained.

Referring again to FIGS. 1-3, when the rear gate on the compressor 52 is opened, the elongated pledget 60 is released and is directed by vacuum or air through a feed tube 62 towards a pair of heat set wheels 64 and 66. The heat set wheels 64 and 66 are rotatably mounted on individual shafts 68 and 70, respectively, and are angularly offset from one another. The heat set wheels 64 and 66 are essentially identical in construction and each contains a plurality of apertures 72 spaced about the outer circumference thereof. Each of the apertures 72 has a diameter which is larger than the diameter of the compressed pledgets 60. The heat set wheels 64 and 66 are designed to be elevated in temperature to a desired value for at least a portion of the 360° cycle so as to heat set the configuration of the pledgets. The temperature can be adjusted between room temperature and about 250° F. Depending upon operational preferences, the apertures 72 into which the elongated pledget 60 is first received can be preheated or alternatively, the apertures 72 can be heated at a later time during the 360 degree rotational cycle of each of the heat set wheels 64 and 66. The heat set wheels 64 and 66 are rotated in an indexing fashion and, at a given indexed position, one of the apertures 72 formed in the first heat set wheel 64 will be coaxially aligned with one of the apertures 72 formed in the second heat set wheel 66. In addition, the two coaxially aligned apertures 72 will be axially aligned with the feed tube 62 and be connected thereto.

Figure 2:
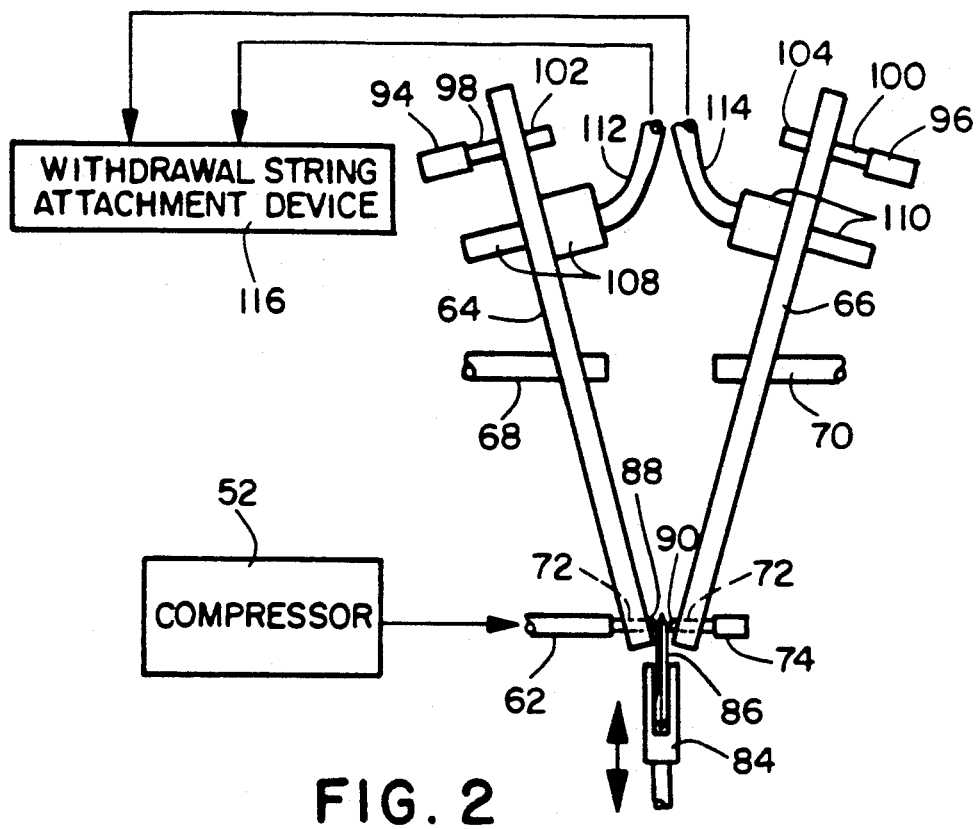
FIG. 2 is a top view of a pair of heat set wheels having a cutter positioned therebetween.
Figure 3:
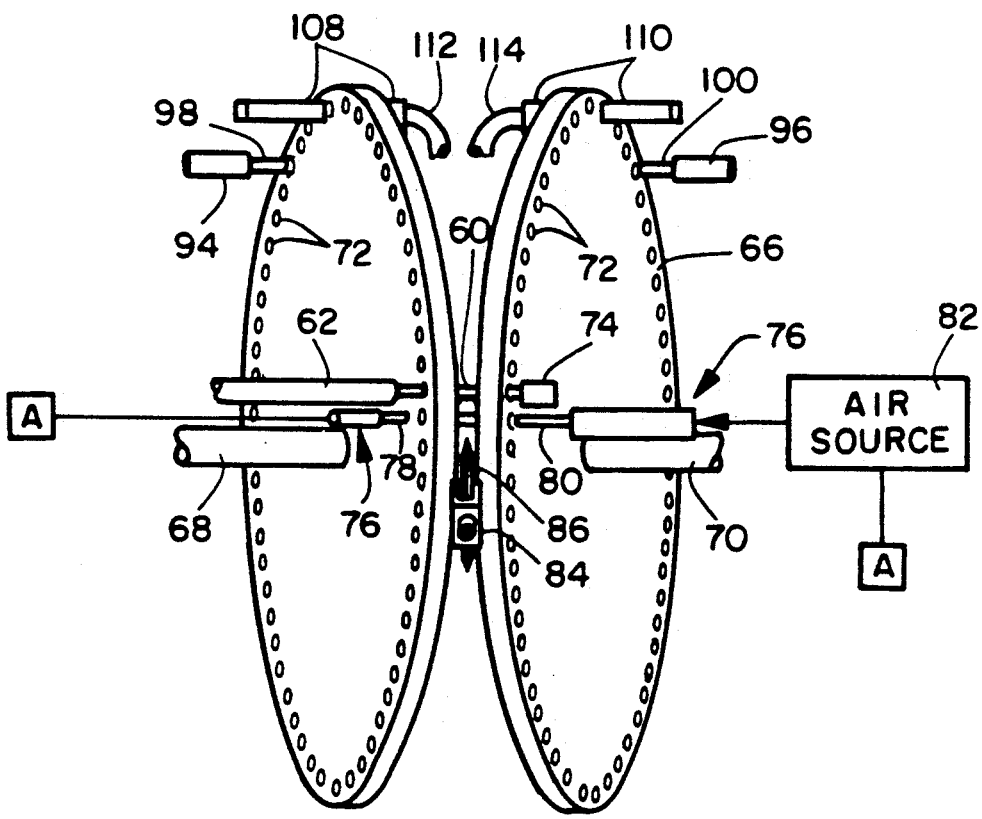
FIG. 3 is a side view of the pair of heat set wheels showing a stop mechanism, a centering mechanism and the cutter position therebetween.

As best shown in FIGS. 2 and 3, each elongated pledget 60 will be fed into the axially aligned apertures 72 formed in both the first and second heat set wheels 64 and 66 and will come to rest against a stop 74. The stop 74 is positioned adjacent to the outside surface of the second heat set wheel 66. When the elongated pledget 60 comes to a stop, it will be positioned across the width of both the first and second heat set wheels 64 and 66. The heat set wheels 64 and 66 are then indexed (rotated a predetermined amount) and the elongated pledget 60 is brought into alignment with a centering device 76. The centering device 76 contains a pair of fingers 78 and 80, each positioned against the outer surface of the heat set wheels 64 and 66, respectively. The fingers 78 and 80 are connected to a source of pressurized air 82 and are pneumatically actuated, such as by air cylinders. It should be noted that other mechanical, electromechanical, hydraulic or pneumatical devices can be utilized as a centering device. The centering device 76 operates by simultaneously moving the fingers 78 and 80 inward a set distance towards the elongated pledget 60. This causes the elongated pledget 60 to be centered between the two heat set wheels 64 and 66.

The two heat set wheels 64 and 66 are then indexed (rotated a predetermined amount) and the elongated pledget 60 is brought into engagement with a cutter 84. The cutter 84 is positioned between the two heat set wheels 64 and 66 and contains a blade 86 which can be rotated in either a clockwise or counter clockwise direction. It should be noted that the cutter 84 can be a conventional cutter, such as a bandsaw or a rotary blade. The cutter 84 can also have one or more rotary blades or movable knifes. Furthermore, a laser, a water jet or an ultrasonic energy device could also be used. The cutter 84 is capable of cutting the elongated pledget 60 into two equal, single length pledgets 88 and 90, as shown in FIG. 6. By "single length" is meant a length approximately equal to the length of the finished tampon. In situations where the elongated pledget 60 is designed to be cut into three or more parts, it is possible to position cutters between several heat set wheels. For example, if one wished to cut an elongated pledget 60 into three parts, one would use three heat set wheels with a cutter positioned between each pair of wheels.

Each of the two single length pledgets 88 and 90 will remain in its respective opening 72 formed in each of the heat set wheels 64 and 66 and will be exposed to a heating operation as the heat set wheels 64 and 66 are rotated. The pledgets 88 and 90 can be heated prior to being cut, after being cut or while being cut if desired. In the heat set operation, the pledgets 88 and 90 acquire a circular cross-sectional diameter expanding slightly from their initial hexagonal shape. The amount of expansion can be adjusted relative to the temperature and the length of time that the pledgets 88 and 90 remain in the apertures 72. The time can be adjusted depending upon the diameter and speed of the heat set wheels 64 and 66. Besides setting the cross-sectional diameter of each pledget, the heating operation also assists in sealing the trailing edge of the cover 92 to the outer surface of the cover strip 20, see FIG. 4. In addition, the heat also bonds the cover strip 20 to the outer circumference of the rolled absorbent ribbon 14.

The heat set wheels 64 and 66 are designed to rotate a predetermined distance, for example about 180°, before the pledgets 88 and 90 are brought into alignment with a pair of nose applicators 94 and 96. The nose applicators 94 and 96 are designed to form a nose or rounded end on one end of each of the pledgets 88 and 90. Each nose applicators 94 and 96 is located adjacent to the outside surface of one of the heat set wheels 64 and 66. Each nose applicator 94 and 96 contains a moveable finger 98 and 100, respectively. The fingers 98 and 100 are arranged to move inward into coaxially alignment with the opening 72. Positioned on the opposite or interior surface of each of the wheels 64 and 66 are a pair of stops 102 and 104. The stops 102 and 104, which are depicted as a pair of rollers in FIG. 3, serve to prevent the pledgets 88 and 90 from being pushed out of the heat set wheels 64 and 66 when the fingers 98 and 100 come in contact with one end of the pledgets 88 and 90. The fingers 98 and 100 are contoured into a semispherical shape such as to form a crown or round portion 106, see FIG. 7, onto the insertion end of each pledget. In the industry, this crown or rounded end is known as a "nose" and the operation of forming it is called "nosing".

It is advantageous to nose each of the pledgets 88 and 90 after they have been heat set and shortly before they are to be withdrawn from the heat set wheels 64 and 66. The reason for the delay in performing the nosing operation is to make sure the pledgets 88 and 90 will not be exposed to a prolong period of heat wherein the shape of the rounded nose could change.

After being nosed, the heat set wheels 62 and 64 are indexed to a position wherein each of the pledgets 88 and 90 are brought into alignment with a pair of ejectors 108 and 110. The ejector 108 and 110 are positioned on the outside of the heat set wheels 62 and 64 which are connected to a vacuum source. When the apertures 72, which house the pledgets 88 and 90 are brought into axial alignment with the ejector 108 and 110, the pledgets 88 and 90 will be sucked out by the vacuum. The pledgets 88 and 90 will be conveyed through feed lines 112 and 114, respectively, to a withdrawal string attachment device 116, see FIGS. 1 and 2.

At the withdrawal string attachment device 116, a pierce and loop method is commonly employed wherein an awl or needle is used to pierce an aperture 118 diagonally through each pledget. The aperture 118, see FIG. 7 can be formed approximate one end of the pledget, usually about ⅛ to ¼ inch from the trailing end. A withdrawal string 120, normally constructed of cotton, rayon, polyester, a blend of rayon and polyester, a polymer or other suitable materials, is then threaded through the aperture 118. The withdrawal string 118 is then looped upon itself to form a loop 122 which secures it to the pledget. It is also common to tie a knot 124 into the free end of the withdrawal string 120. It should be noted that there are many different ways of attaching the withdrawal string 120 to a pledget. Some of these methods are taught in U.S. Pat. Nos. 2,553,000 at column 2, lines 39–48; 2,529,183; 4,302,174; and 4,318,407. The teachings of these patents are incorporated by reference and made a part hereof. In addition, the withdrawal string 120 could be attached by wrapping it about the absorbent material 14 before the softwind 46 is compressed.

Referring to FIG. 7, a finished tampon 126 is shown having an insertion end 128 and a trailing end 130. The insertion end 128 is the end which is first inserted into a woman's vagina and it is located opposite to the trailing end 130.

Referring to FIG. 8, the finished tampon 126 is directed to a packaging operation 132, see FIG. 1, wherein it is wrapped. The wrapper can be a pouch made out of a polymer, such as polyethylene, polypropylene, ethyl vinyl acetate, or other suitable material. The wrapped pouches are then placed in a cardboard box or a plastic bag for distribution to the ultimate consumer. Optionally, the finished tampon 126 can be directed to an assembly operation 134, wherein it is assembled into a tampon applicator 136, see FIG. 8. The tampon applicator 136 consists of a hollow outer tube 138 having an insertion end 140 on which a plurality of petals 142 can be formed. A pusher tube 144, having a smaller diameter than the outer tube 138, is telescopically received within the outer tube 138 and can move relative thereto. The tampon 126 is positioned in the outer tube 138 with the withdrawal string 120 passing through the pusher tube 144 and extending outward therefrom. Various types of tampon applicators are known in the art and they can be made from various materials including cardboard, paper or plastic.

Figure 9:
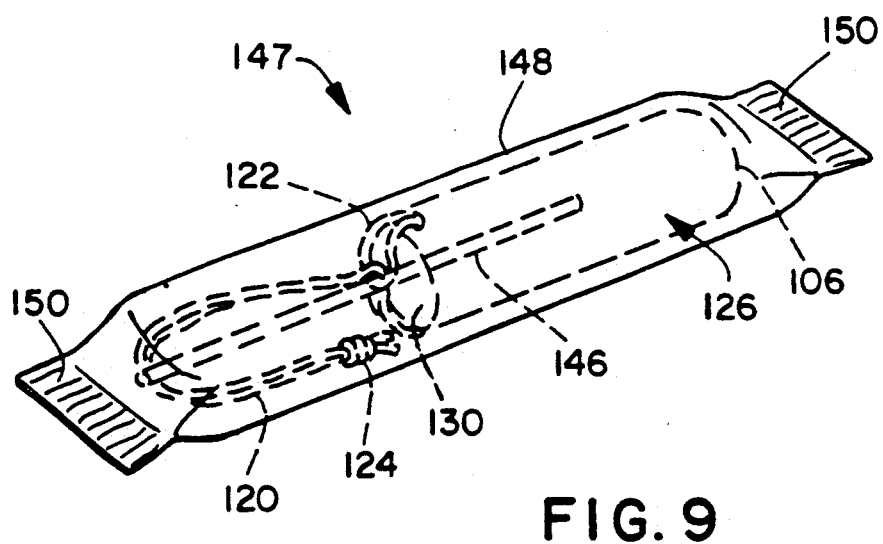
FIG. 9 is a schematic view of a stick tampon packaged in a thermoplastic pouch.

Referring to FIG. 9, the tampon 126 can also have a stick 146 inserted into its trailing end 130 to form a stick tampon 147. The stick tampon 147 can be enclosed in a paper or plastic wrapper 148. The wrapper 148 is sealed at 150 on one or both ends.

Figure 10:
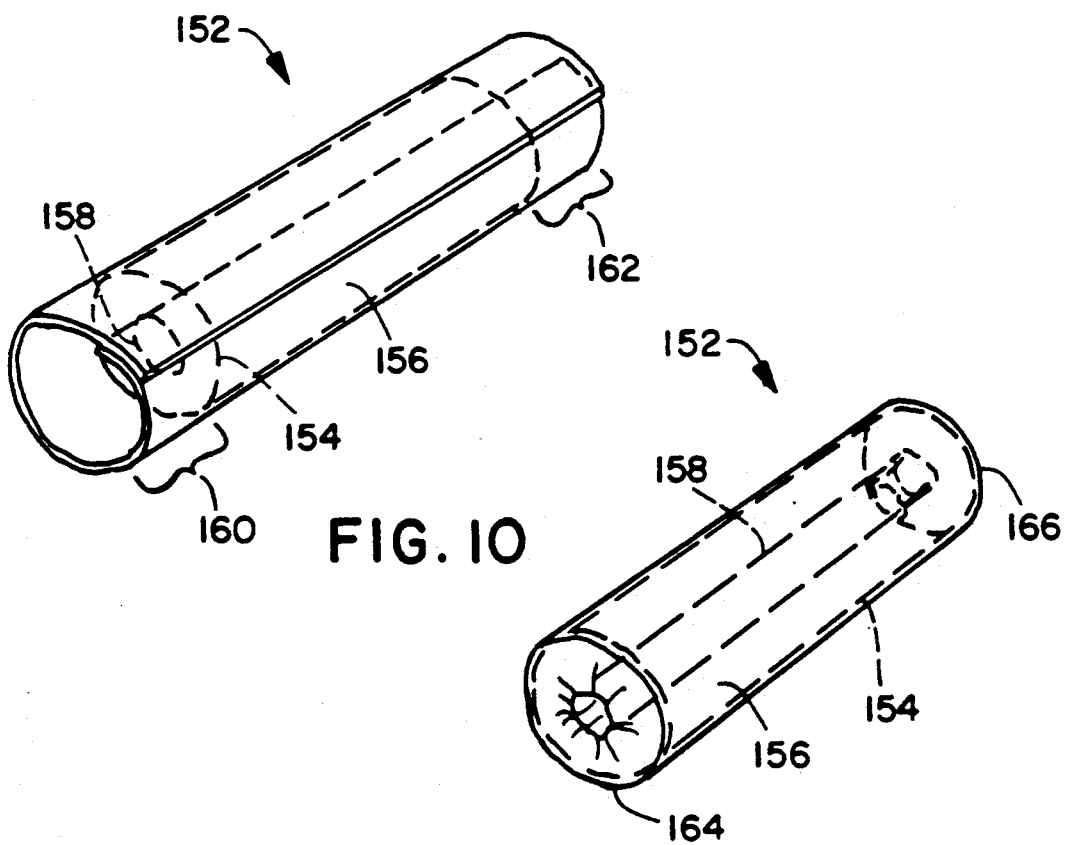
FIG. 10 is a perspective view of a softwind wherein the cover strip has a longer width than the absorbent ribbon so that it can be tucked into one or both ends of the absorbent ribbon to form a covered tampon.
Figure 11:
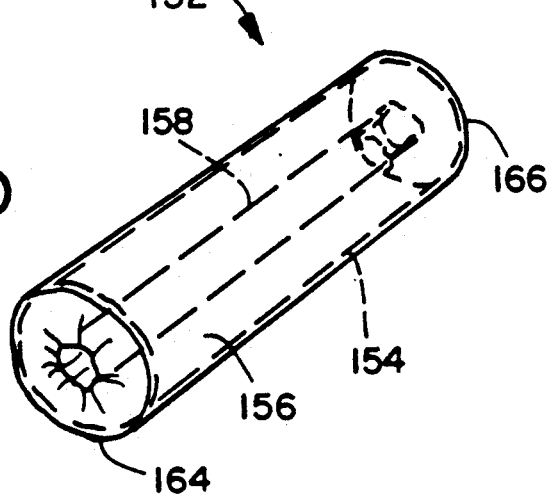
FIG. 11 is a perspective view of an elongated pledget having the cover tucked into both ends of the radially wound absorbent ribbon.
Figure 12:
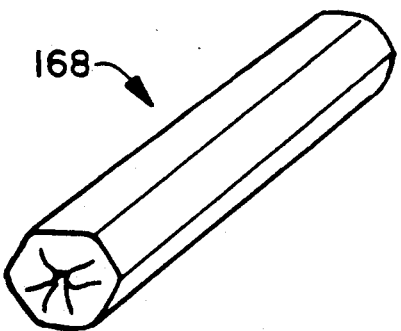
FIG. 12 is a perspective view of a compressed elongated pledget formed from the softwind shown in FIG. 11.
Figure 13:
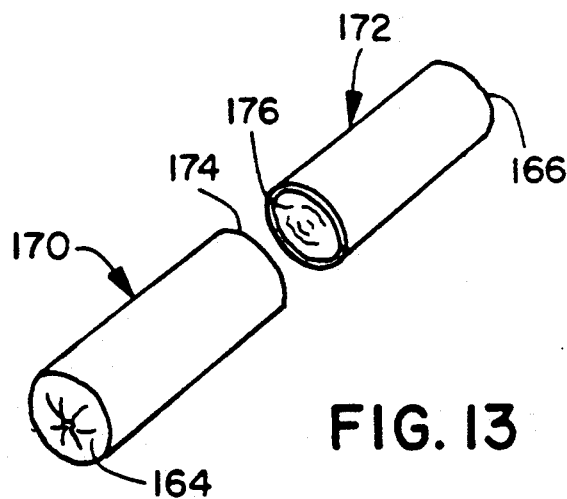
FIG. 13 is a perspective view of two single length pledgets each having a tucked end and an untucked end.

Referring to FIGS. 10 and 11, a cylinder or softwind 152 is shown consisting of an absorbent ribbon 154 radially wound upon itself and enclosed by a cover strip 156. The softwind 152 contains an opening 158 formed therethrough and the initial width of the cover strip 156 is shown being longer than the initial width of the absorbent ribbon 154. This size difference causes sleeves 160 and 162 to be formed on each end of the softwind 152. The sleeves 160 and 162 can vary in size but enough cover material 156 should be present to permit the cover strip 156 to be tucked into either end of the opening 158. In FIG. 11, the softwind 152 is shown having two tucked ends 164 and 166.

Figure 16:
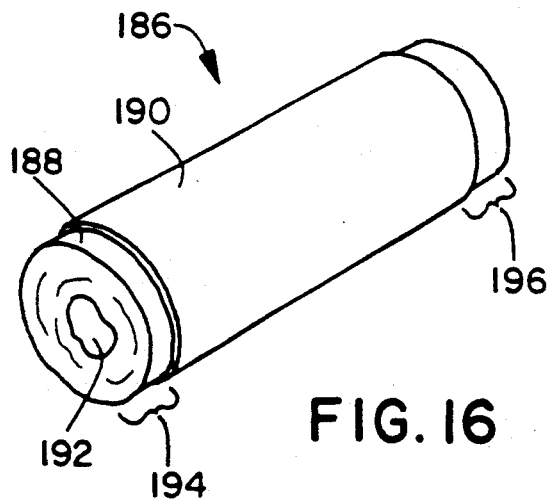
FIG. 16 is a perspective view of a radially wound absorbent ribbon showing a cover having an initial width which is less than the initial width of the absorbent ribbon such that it does not extend to either end of the absorbent ribbon.
Figure 17:
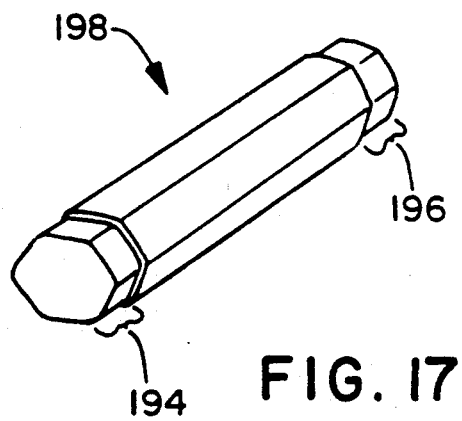
FIG. 17 is a perspective view of a compressed hexagonal shaped pledget made from the radially wound softwind shown in FIG. 16.
Figure 18:
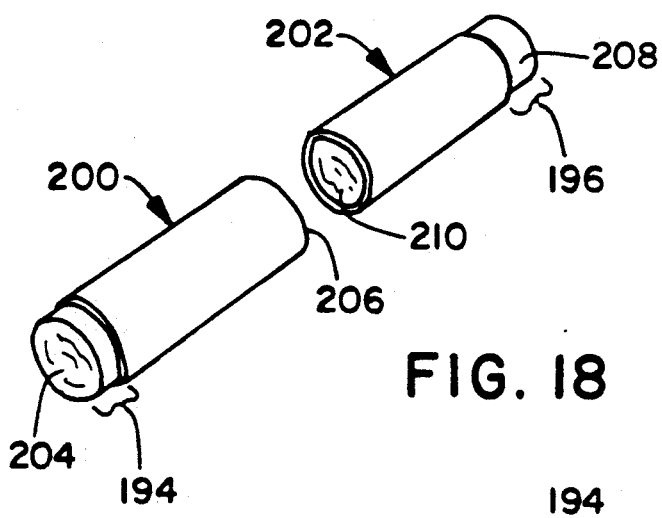
FIG. 18 is a perspective view of two single length pledgets showing the cover surrounding the outer circumference of the absorbent ribbon and being spaced apart from the insertion end and being aligned even with the trailing end.

Referring to FIGS. 12–15, the softwind 152 is compressed to form an elongated pledget 168 having a hexagonal configuration. The elongated pledget 168 is then cut into two single length pledgets 170 and 172, see FIG. 13. Each pledget 170 and 172 has an untucked end 174 and 176, respectively, which exhibits exposed absorbent ribbon. Normally, the insertion end will be rounded to form a nose 178 and a withdrawal string 120 can be attached to the trailing end, as explained above, to provide a finished tampon 180, see FIG. 14. Optionally, the untucked end 174 can be rounded to form a nose 182, see FIG. 15. Referring to FIGS. 16–18, an alternative embodiment is shown wherein a softwind 186 is composed of a radially wound absorbent ribbon 188 and a cover strip 190. The softwind 186 has a large opening 192 formed therethrough. In this embodiment, the cover strip 190 has the initial width which is less than the initial width of the absorbent ribbon 188 and therefore a cylindrical cuff 194 and 196 is formed on each end of the softwind 186. The cylindrical cuffs 194 and 196 exhibits absorbent ribbon 188 which is uncovered. The softwind 186 is then compressed into an elongated pledget 198, see FIG. 16. The elongated pledget 198 is then cut into two equal, single length pledgets 200 and 202. The pledget 200 will contain a cuffed first end 204 and an uncuffed trailing end 206. The first end 204, which will preferably be the insertion end, will be surrounded by the exposed ribbon 194. The other single length pledget 202 will contain a cuffed first end 208 and a trailing end 210. The first end 208 will be surrounded by the exposed absorbent ribbon 196.

Figure 19:
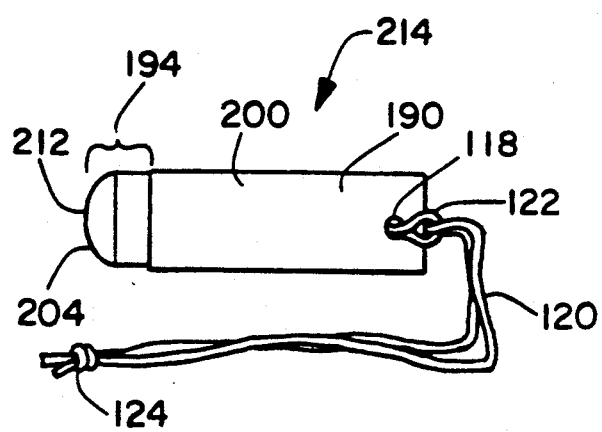
FIG. 19 is a side view of a pledget having a rounded insertion end with the cover strip spaced away from this end to form a cuff.

Referring to FIG. 19, the first end 204 of the pledget 200 is rounded to form a nose 212. This nose 212 primarily contains exposed absorbent ribbon 194. While either end of the pledget can be nosed, it is now possible to form an uncovered nose on a cylindrically covered tampon. A withdrawal string 120 can then be attached to the pledget 200, as explained above, to form a finished tampon 214.

It should be noted that the configurations of the above-described tampons 126, 180, 184 and 214 are made possible by the use of absorbent materials which contain enough integrity and structure so that they can be inserted into a woman's vagina without being partially or fully covered by a cover strip.

While the invention has been described in conjunction with several specific embodiments, it is to be understood that many alternatives, modifications, and variations will be apparent to those skilled in the art in light of the aforegoing description. Accordingly, this invention is intended to embrace all such alternatives, modifications and variations which fall within the spirit and scope of the appended claims.

We claim:
1. An apparatus for forming tampons comprising:
   a) means for advancing and cutting a liquid permeable cover strip and an absorbent ribbon into defined lengths;
   b) means for positioning an individual length of said cover strip over a portion of an individual length of said ribbon;
   c) means for attaching said cover strip to said overlapped portion of said ribbon;
   d) means for rolling said ribbon and said cover strip into a cylinder with said cover strip encircling the outer circumference thereof and having a length corresponding to the length of at least two tampons;
   e) means for compressing said cylinder into an elongated pledget;
   f) means for cutting said elongated pledget into at least two single length pledgets;

g) means for heat setting said single length pledgets to obtain a desired configuration; and
h) means for attaching a withdrawal string to each of said single length pledgets to form tampons.

2. The apparatus of claim 1 wherein said elongated pledget is cut into two equal lengths by said cutting means.

3. The apparatus of claim 1 wherein said means for cutting said pledget is a rotary blade.

4. The apparatus of claim 1 wherein said means for heat setting said pledgets consist of a pair of rotatable wheels coaxially aligned and angularly offset from one another.

5. The apparatus of claim 4 wherein each of said wheels contains a plurality of openings spaced about the outer circumference thereof, and at least in one position, an opening in one wheel is axially aligned with an opening in said other wheel so as to define means for receiving said elongated pledget.

6. The apparatus of claim 5 wherein said pair of wheels contain means for centering the elongated pledget which is received in said coaxially aligned pair of openings in said at least one position.

7. The apparatus of claim 6 wherein said means for cutting includes a cutter positioned between said pair of wheels which is capable of cutting an elongated pledget positioned within said coaxially aligned openings in said at least one position and centered therebetween as said wheels are indexed past said cutter.

8. The apparatus of claim 4 wherein each of said wheels includes means for heating said pledgets positioned within said openings.

9. The apparatus of claim 1 wherein the initial width of said cover strip is longer than the initial width of said absorbent ribbon.

10. The apparatus of claim 9 further including means for sequentially tucking said cover strip into opposite ends of said ribbon.

11. An apparatus for forming tampons comprising:
(a) means for advancing and cutting a liquid permeable cover strip and an absorbent ribbon into defined lengths;
(b) means for positioning and attaching an individual length of said cover strip over a portion of each length of said ribbon;
(c) means for rolling said ribbon and said cover strip into a cylinder with said cover strip encircling the outer circumference thereof and having a length corresponding to the length of two tampons;
(d) means for compressing said cylinder into an elongated pledget;
(e) a pair of rotatable heat set wheels;
(f) means for transferring said elongated pledget into said pair of heat set wheels;
(g) means for cutting said elongated pledget into two single length pledgets while said elongated pledget is being rotated by said heat set wheels; and
(h) means for attaching a withdrawal string to each of said single length pledgets to form tampons.

12. The apparatus of claim 11 further including means for centering said elongated pledget in said pair of heat set wheels and said means for cutting cuts said elongated pledget into two equal lengths.

13. The apparatus of claim 12 wherein said centering means is a pneumatic device positioned adjacent to said pair of wheels.

14. The apparatus of claim 11 further including means for exposing said elongated pledget to an elevated temperature in said heat set wheels before being cut into at least two single length pledgets.

15. The apparatus of claim 11 further including means for exposing said elongated pledget to an elevated temperature in said heat set wheels after said elongated pledget is cut into at least two single length pledgets.

16. The apparatus of claim 11 further including means for heating said pair of heat set wheels to a temperature between room temperature and 250° F.

17. A method of forming tampons comprising the steps of:
(a) positioning a liquid permeable cover strip over a portion of a non-woven absorbent ribbon;
(b) attaching said cover strip to said overlapped portion of said ribbon;
(c) rolling said ribbon and cover strip into a cylinder with said cover strip encircling the outer circumference thereof and having a length corresponding to the length of at least two tampons;
(d) compressing said cylinder into an elongated pledget;
(e) cutting said elongated pledget into at least two single length pledgets;
(f) heat setting said single length pledgets to obtain a desired configuration; and
(g) attaching a withdrawal string to each of said single length pledgets to form tampons.

18. The method of claim 17 wherein the step of cutting includes cutting said elongated pledget into two equal length pledgets.

19. The method of claim 17 wherein the step of heat setting further includes rounding one end of each single length pledget.

20. The method of claim 17 wherein the step of cutting includes cutting said elongated pledget into at least two single length pledgets with a rotary blade.

21. The method of claim 17 further including the step of forming an aperture through each single length pledget approximate one end thereof and said step of attaching includes passing a withdrawal string through said aperture and looping it about itself to form a secure attachment.

22. The method of claim 17 further including the step of assembling each of said tampons into an applicator.

23. A method of forming two tampons simultaneously comprising the steps of:
(a) positioning a liquid permeable cover strip over a portion of a non-woven absorbent ribbon;
(b) attaching said cover strip to said overlapped portion of said ribbon using heat and pressure;
(c) rolling said ribbon and said cover strip into a cylinder with said cover strip completely encircling the outer circumference thereof and having a length corresponding to the length of at least two tampons;
(d) compressing said cylinder into an elongated pledget;
(e) cutting said elongated pledget into two single length pledgets;
(f) heat setting said single length pledgets to obtain a desired diameter and bond said cover strip to the outer circumference thereof; and
(g) attaching a withdrawal string to each of said single length pledgets to form tampons.

24. The method of claim 23 further including the step of tucking said cover strip into said rolled up ribbon before said cylinder is compressed.

25. The method of claim 23 wherein the step of rolling includes radially winding said ribbon and said cover strip together.

26. The method of claim 23 further including the step of centering said elongated pledget relative to a cutter prior to cutting and said step of cutting includes cutting said elongated pledget into two equal length pledgets.

27. The method of claim 23 further including the step of assembling each of said tampons into an applicator having a hollow outer tube and a pusher tube by positioning said tampon in said outer tube and said withdrawal string passing through said pusher tube and extending outward therefrom.

28. The method of claim 23 further including the step of forming an aperture through each single length pledget approximate one end thereof and said step of attaching includes passing a withdrawal string through said aperture and looping it about itself to form a secure attachment.

29. The method of claim 23 wherein said cylinder has an initial diameter and the step of compressing includes compressing said cylinder into an elongated pledget having a diameter which is at least 25 percent smaller than said initial diameter.

30. A method of forming multiple tampons comprising the steps of:
(a) positioning a rectangularly shaped cover strip over a portion of a rectangular absorbent ribbon;
(b) attaching said cover strip to said overlapped portion of said ribbon using heat and pressure;
(c) rolling said ribbon and said cover strip into a cylinder with said cover strip encircling the outer circumference thereof and having a length corresponding to the length of at least two tampons;
(d) compressing said cylinder into a smaller diameter elongated pledget;
(e) cutting said elongated pledget into a desired number of single length pledgets;
(f) heat setting said single length pledgets to create a desired profile and to bond said cover strip to the outer circumference thereof; and
(g) attaching a withdrawal string to each of said single length pledgets to form tampons.

31. The method of claim 30 wherein said cylinder has an initial diameter and the step of compressing includes compressing said cylinder into an elongated pledget having a diameter which is at least 50 percent less than said initial diameter.

32. The method of claim 31 wherein the step of compressing includes compressing said cylinder into an elongated pledget having a diameter which is at least 100 percent less than said initial diameter.

33. The method of claim 30 wherein the step of cutting includes cutting said compressed elongated pledget into three equal length pledgets.

* * * * *